(12) United States Patent
Wideman et al.

(10) Patent No.: US 6,218,561 B1
(45) Date of Patent: Apr. 17, 2001

(54) PROCESS FOR THE PREPARATION OF BIS ORGANOSILICON DISULFIDE COMPOUNDS

(75) Inventors: Lawson Gibson Wideman, Hudson; Theodore Lamson Folk, Cuyahoga Falls, both of OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/603,327

(22) Filed: Jun. 26, 2000

(51) Int. Cl.$^7$ .................................................. C07F 7/08
(52) U.S. Cl. .................................... 556/427; 548/110
(58) Field of Search ............................ 556/427; 548/110

(56) References Cited

U.S. PATENT DOCUMENTS

| 5,663,358 | 9/1997 | Cohen et al. | 548/166 |
| 5,675,014 | 10/1997 | Cohen et al. | 548/110 |
| 5,684,172 | * 11/1997 | Wideman et al. | 556/427 |
| 6,093,829 | * 7/2000 | Berger et al. | 548/110 |

* cited by examiner

Primary Examiner—Paul F. Shaver
(74) Attorney, Agent, or Firm—Bruce J Hendricks

(57) ABSTRACT

The present invention relates to a process for the preparation of organo silicon disulfide compounds. The process involves reacting a mercaptoalkoxysilane with a N-alkyl bis (benzothiazolsulfen) amide.

11 Claims, No Drawings

PROCESS FOR THE PREPARATION OF BIS ORGANOSILICON DISULFIDE COMPOUNDS

BACKGROUND OF THE INVENTION

The present invention relates to a process for the preparation of organosilicon disulfide compounds. Organosilicon disulfides are known adhesion promoters in sulfur-vulcanizable rubber mixtures reinforced with inorganic materials such as glass SiO2, aluminosilicates and carbon black. For example, in GB 1,484,909, there is disclosed a process for the preparation of organo trialkoxysilane disulfides. In accordance with the teachings of this reference, mercaptopropyl trimethoxy silane or mercaptopropyl triethoxy silane is reacted with sulfuryl chloride in an inert solvent at temperatures of from 0° to 100°. The disulfide is then obtained by fractional distillation. The yields of desired product range in the neighborhood of 63 to 65 percent of theoretical.

U.S. Pat. No. 3,842,111 discloses a method for the preparation of organosilicon disulfide compounds by oxidizing mercaptoalkoxysilanes. Representative oxidizing agents include oxygen, chlorine, halogens of atomic weight 35 to 127, nitric oxide, sulfuryl chloride and sulfoxides.

U.S. Pat. No. 5,675,014 relates to a process for the preparation of organosilicon disulfide compounds by reacting a mercaptoalkoxysilane with a dithiobis (benzothiazole) compound. Unfortunately, this process does not produce high purity bis organosilicon disulfide compounds due to the formation of unsymmetrical organosilicon disulfides.

U.S. Pat. No. 5,663,358 relates to a process for the preparation of organosilicon disulfide compounds by reacting a mercaptoalkoxysilane with a sulfenamide compound. Unfortunately, due to the formation of unsymmetrical organosilicon compounds, the purity of bis organosilicon disulfide compounds are reduced.

Generally speaking, bis organosilicon disulfide compounds are very expensive and, with the increasing interest in silica-reinforced vulcanizable rubber, more cost-efficient methods of preparing these compounds are needed.

SUMMARY OF THE INVENTION

The present invention relates to a process for the preparation of bis organosilicon disulfide compounds. The present invention may be used to prepare symmetrical organosilicon disulfide compounds of the formula:

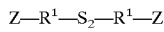

I wherein Z is selected from the group consisting of

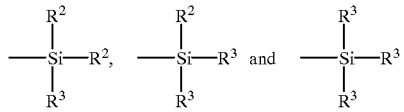

wherein $R^2$ may be the same or different and is independently selected from the group consisting of an alkyl group having 1 to 4 carbons and phenyl; $R^3$ may be the same or different and is independently selected from the group consisting of alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

DETAILED DESCRIPTION OF THE INVENTION

There is disclosed a process for the preparation of bis organosilicon disulfide compounds comprising reacting (a) the N-alkyl bis (benzothiazolsulfen) amide of the formula

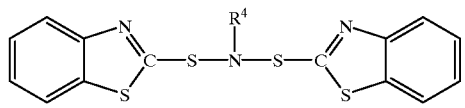

II with (b) mercaptosilane compound of the formula

       III wherein Z is selected from the group consisting of

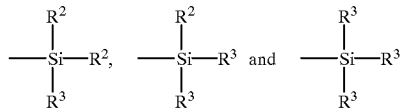

wherein R1 is selected from the group consisting of a substituted or unsubstituted alkylene group having a total of 1 to 18 carbon atoms and a substituted or unsubstituted arylene group having a total of 6 to 12 carbon atoms; wherein $R^2$ may be the same or different and is independently selected from the group consisting of an alkyl group having 1 to 4 carbons and phenyl; $R^3$ may be the same or different and is independently selected from the group consisting of alkoxy groups having 1 to 8 carbon atoms and cycloalkoxy groups with 5 to 8 carbon atoms; and $R^4$ is an alkyl group having from 3 to 6 carbon atoms.

The present invention relates to a process for the preparation of bis organosilicon disulfide compounds. Representative organosilicon disulfide compounds of formula I which may be prepared in accordance with the present invention include 2,2'-bis(trimethoxysilylethyl) disulfide; 3,3'-bis (trimethoxysilylpropyl) disulfide; 3,3'-bis (triethoxysilylpropyl) disulfide; 2,2'-bis (triethoxysilylpropyl) disulfide; 2,2'-bis (tripropoxysilylethyl) disulfide; 2,2'-bis(tri-sec-butoxysilylethyl) disulfide; 2,2'-bis(tri-t-butoxysilylethyl) disulfide; 3,3'-bis(triisopropoxysilylpropyl) disulfide; 3,3'-bis(trioctoxysilylpropyl) disulfide; 2,2'-bis(2'-ethylhexoxysilylethyl) disulfide; 2,2'-bis(dimethoxy ethoxysilylethyl) disulfide; 3,3'-bis (methoxyethoxypropoxysilylpropyl) disulfide; 3,3'-bis (dimethoxymethylsilylpropyl) disulfide; 3,3'-bis(methoxy dimethylsilylpropyl) disulfide; 3,3'-bis (diethoxymethylsilylpropyl) disulfide, 3,3'-bis(ethoxy dimethylsilylpropyl) disulfide, 3,3'-bis(cyclohexoxy dimethylsilyipropyl) disulfide; 4,4'-bis (trimethoxysilylbutyl) disulfide; 3,3'-bis(trimethoxysilyl-3-methylpropyl) disulfide; 3,3'-bis(tripropoxysilyl-3-methylpropyl) disulfide; 3,3'-bis(dimethoxy methylsilyl-3-ethylpropyl) disulfide; 3,3 '-bis(trimethoxysi lyl-2-methylpropyl) disulfide; 3,3 '-bis(dimethoxyphenylsilyl-2-methylpropyl) disulfide; 3,3 '-bis (trimethoxysilylcyclohexyl) disulfide; 12,12'-bis (trimethoxysilyldodecyl) disulfide; 12,12'-bis (triethoxysilyldodecyl) disulfide; 18,18'-bis (trimethoxysilyloctadecyl) disulfide; 18,18'-bis (methoxydimethylsilyloctadecyl) disulfide; 2,2'-bis (trimethoxysilyl-2-methylethyl) disulfide; 2,2'-bis (tripropoxysilyl-2-methylethyl) disulfide; 2,2'-bis (trioctoxysilyl-2-methylethyl) disulfide; 2,2'-bis (trimethoxysilyl-phenyl) disulfide; 2,2'-bis(triethoxysilyl-phenyl) disulfide; 2,2'-bis(trimethoxysilyl-tolyl)disulfide; 2,2'-bis(triethoxysilyl-tolyl)disulfide; 2,2'-bis (trimethoxysilyl-methyl tolyl) disulfide; 2,2'-bis (triethoxysilyl-methyl tolyl) disulfide; 2,2'-bis (trimethoxysilyl-ethyl phenyl) disulfide; 2,2'-bis (triethoxysilyl-ethyl phenyl) disulfide; 2,2'-bis (trimethoxysilyl-ethyl tolyl) disulfide; 2,2'-bis (triethoxysilyl-ethyl tolyl) disulfide; 3,3'-bis (trimethoxysilyl-propyl phenyl) disulfide; 3,3'-bis (triethoxysilyl-propyl phenyl) disulfide; 3,3'-bis (trimethoxysilyl-propyl tolyl) disulfide; and 3,3'-bis (triethoxysilyl-propyl tolyl) disulfide.

With reference to formula I, preferably $R^1$ is a alkylene group having 2 to 3 carbon atoms, Z is 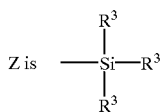

and $R^3$ is an alkoxy group having from 1 to 3 carbon atoms.

The desired products are prepared by reacting the N-alkyl bis (benzothiazolesulfen) amide compound of formula II with a mercaptosilane compound of formula III. Representative examples of compounds of formula III include 2-mercaptoethyl trimethoxysilane, 3-mercaptopropyl trimethoxysilane, 3-mercaptopropyl triethoxysilane, 2-mercaptopropyl triethoxysilane, 2-mercaptoethyl tripropoxysilane, 2-mercaptoethyl tri sec-butoxysi lane, 3-mercaptopropyl tri-t-butoxysi lane, 3-mercaptopropyl tri-isopropoxysi lane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl ethoxy dimethylsilane, 3-mercaptopropyl diethoxy methylsilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysi lane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptoctadecyl trimethoxysilane, 18-mercaptooctadecyl methoxydimethylsilane, 2-mercapto-2-methylethyl-tripropoxysilane, 2-mercapto-2-methylethyl-trioctoxysilane, 2-mercaptophenyl trimethoxysilane, 2-mercaptophenyl triethoxysilane; 2-mercaptotolyl trimethoxysilane; 2-mercaptotolyl triethoxysilane; 1-mercaptomethyltolyl trimethoxysilane; 1-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

With reference to formula III, preferably Z is

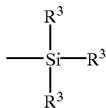

$R^4$ is an alkoxy group having from 1 to 3 carbon atoms and $R^1$ is an alkylene group having 2 to 3 carbon atoms.

The molar ratio of the compound of formula II to the compound of formula III may range from 1:5 to 5:1. Preferably, the molar ratio ranges from 1:3 to 3:1 with a range of from 1:1 to 1:2 being particularly preferred.

The reaction should be conducted in the absence of water because the presence of an alkoxysilane moiety may be hydrolysed by contact with water.

The reaction of the present invention may be conducted in the presence of an organic solvent. Suitable solvents which may be used include chloroform, dichloromethane, carbon tetrachloride, hexane, heptane, cyclohexane, xylene, benzene, dichloroethylene, trichloroethylene, dioxane, diisopropyl ether, tetrahydrofuran and toluene. As indicated above, care should be exercised to avoid the presence of water during the reaction. Therefore, none of the above solvent should contain any appreciable levels of water. Preferably, the organic solvent is chloroform, heptane, cyclohexane, xylene and toluene.

The reaction may be conducted over a variety of temperatures. Generally speaking, the reaction is conducted in a temperature ranging from 20° C. to 140° C. Preferably, the reaction is conducted at a temperature ranging from 25° C. to 50° C.

The process of the present invention may be conducted at a variety of pressures. Generally speaking, however, the reaction is conducted at a pressure ranging from 0.096 to 4.83 kg/cm2.

EXAMPLE 1

Preparation of High Purity 3,3'-Bis(3-Triethoxvsilvlpropvl) Disulfide

A 1 quart (0.945 liter) glass reactor was charged with 800 ml of toluene, 47.68 g (0.20 mole) of 3-mercaptopropyltriethoxysilane, 80.6 g (0.20 mole) of N-tert-butyl-bis-2(2-benzothiazolesulfen) amide with stirring. The reactor was flushed with nitrogen and stirred for 24 hours at room temperature. The solution was filtered free of particles and the solvent distilled away under reduced pressure. The resulting liquid was shown by Mass Spectrometry analysis to be high purity 3,3'-bis(triethoxysilylpropyl) disulfide (99+percent) as the only disulfide reaction product.

What is claimed is:
1. A process for the preparation of bis organosilicon disulfide compounds comprising reacting

(a) a N-alkyl bis(benzothiazolesulfen) amide compound of the formula

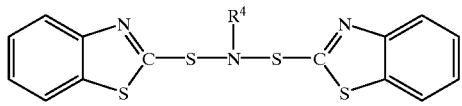

with (b) mercaptosilane compound of the formula

Z—R¹—SH      III wherein Z is selected from the group consisting of

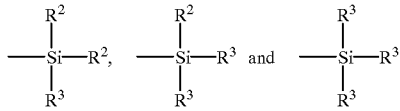

wherein $R^1$ is selected from the group consisting of a substituted or unsubstituted alkylene group having a total of 1 to 18 carbon atoms and a substituted or unsubstituted arylene group having a total of 6 to 12 carbon atoms; wherein $R^2$ may be the same or different and is independently selected from the group consisting of an alkyl group having 1 to 4 carbons and phenyl; $R^3$ may be the same or different and is independently selected from the group consisting of alkoxy groups having 1 to 8 carbon atoms and cycloalkoxy groups with 5 to 8 carbon atoms; and $R^4$ is an alkyl group having from 3 to 6 carbon atoms.

2. The process of claim 1 wherein

Z is 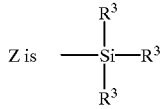

$R^3$ selected from the group consisting of alkoxy groups having 1 to 3 carbon atoms and $R^1$ is an alkylene group having 2 to 3 carbon atoms.

3. The process of claim 1 wherein the molar ratio of the compound of formula II to the compound of formula III ranges from 1:5 to 5:1.

4. The process of claim 3 wherein the molar ratio of the compound of formula II to the compound of formula II ranges from 1:3 to 3:1.

5. The process of claim 1 wherein said bis organosilicon disulfide compounds are of the formula:

Z—R¹—S₂—R¹—Z      I wherein Z is selected from the group consisting of

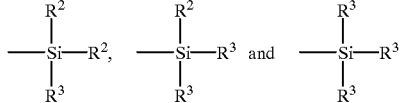

wherein $R^2$ may be the same or different and is independently selected from the group consisting of an alkyl group having 1 to 4 carbons and phenyl; $R^3$ may be the same or different and is independently selected from the group consisting of alkoxy groups having 1 to 8 carbon atoms and cycloalkoxy groups with 5 to 8 carbon atoms; and $R^1$ is selected from the group consisting of a substituted or unsubstituted alkylene group having a total of 1 to 18 carbon atoms and a substituted or unsubstituted arylene group having a total of 6 to 12 carbon atoms.

6. The process of claim 5 wherein said disulfide of formula I is selected from the group consisting of 2,2'-bis (trimethoxysilylethyl) disulfide; 3,3'-bis (trimethoxysilylpropyl) disulfide; 3,3'-bis (triethoxysilylpropyl) disulfide; 2,2'-bis (tripropoxysilylethyl) disulfide; 2,2'-bis (triethoxysilylpropyl) disulfide; 2,2'-bis-tri-sec-butoxysilylethyl) disulfide; 2,2'-bis(tri-t-butoxyethyl) disulfide; 3,3'-bis(triisopropoxysilylpropyl) disulfide; 3,3'-bis(trioctoxysilylpropyl) disulfide; 2,2'-bis(2'-ethylhexoxysilylethyl) disulfide; 2,2'-bis(dimethoxy ethoxysilylethyl) disulfide; 3,3'-bis (methoxyethoxypropoxysilylpropyl) disulfide; 3,3'-bis (dimethoxymethylsilylpropyl) disulfide; 3,3'-bis(methoxy dimethylsilylpropyl) disulfide; 3,3'-bis (diethoxymethylsilylpropyl) disulfide; 3,3'-bis(ethoxy-dimethylsitylpropyl) disulfide; 3,3'-bis(cyclohexoxy dimethylsilylpropyl) disulfide; 4,4'-bis (trimethoxysilylbutyl) disulfide; 3,3'-bis(trimethoxysilyl-3-methylpropyl) disulfide; 3,3'-bis(tripropoxysilyl-3-methylpropyl) disulfide; 3,3'-bis(dimethoxy methylsilyl-3-ethylpropyl) disulfide; 3,3'-bis(trimethoxysilyl-2-methylpropyl) disulfide; 3,3'-bis(dimethoxyphenylsilyl-2-methylpropyl) disulfide; 3,3'-bis (trimethoxysilylcyclohexyl) disulfide; 12,12'-bis (trimethoxysilyldodecyl) disulfide; 12,12'-bis (triethoxysilyldodecyl) disulfide; 18,18'-bis (trimethoxysilyloctadecyl) disulfide; 18,18'-bis (methoxydimethylsilyloctadecyl) disulfide; 2,2'-bis (trimethoxysilyl-2-methylethyl) disulfide; 2,2'-bis (tripropoxysilyl-2-methylethyl) disulfide; 2,2'-bis (trioctoxysilyl-2-methylethyl) disulfide; 2,2'-bis (trimethoxysilyl-phenyl) disulfide; 2,2'-bis(triethoxysilyl-phenyl) disulfide; 2,2'-bis(trimethoxysilyl-tolyl)disulfide; 2,2'-bis(triethoxysilyl-tolyl)disulfide; 2,2'-bis (trimethoxysilyl-methyl tolyl) disulfide; 2,2'-bis (triethoxysilyl-methyl tolyl) disulfide; 2,2'-bis (trimethoxysilyl-ethyl phenyl) disulfide; 2,2'-bis (triethoxysilyl-ethyl phenyl) disulfide; 2,2'-bis (trimethoxysilyl-ethyl tolyl) disulfide; 2,2'-bis (triethoxysilyl-ethyl tolyl) disulfide; 3,3'-bis (trimethoxysilyl-propyl phenyl) disulfide; 3,3'-bis (triethoxysilyl-propyl phenyl) disulfide; 3,3'-bis (trimethoxysilyl-propyl tolyl) disulfide; and 3,3'-bis (triethoxysilyl-propyl tolyl) disulfide.

7. The process of claim 1 wherein said mercaptosilane compound of formula III is selected from a group consisting of 2-mercaptoethyl trimethoxysilane, 3-mercaptopropyl tri methoxysi lane, 2-mercaptopropyl triethoxysi lane, 3-mercaptopropyl triethoxysi lane, 2-mercaptoethyl tripropoxysilane, 2-mercaptoethyl tri sec-butoxysilane, 3-mercaptopropyl tri-t-butoxysilane, 3-mercaptopropyl tri-isopropoxysilane; 3-mercaptopropyl trioctoxysilane, 2-mercaptoethyl tri-2'-ethylhexoxysilane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl ethoxy dimethylsilane, 3-mercaptopropyl diethoxy methylsilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyl-tripropoxysilane, 2-mercapto-2-methylethyl-trioctoxysilane, 2-mercaptophenyl trimethoxysilane, 2-mercaptophenyl triethoxysilane; 2-mercaptotolyl trimethoxysilane; 2-mercaptotolyl triethoxysilane; 1-mercaptomethyltolyl trimethoxysilane; 1-mercaptomethyltolyl triethoxysilane; 2-mercaptoethylphenyl trimethoxysilane; 2-mercaptoethyiphenyl triethoxysi lane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

8. The process of claim 1 wherein said reaction is in absence of water and in the presence of an organic solvent selected from the group consisting of chloroform, dichloromethane, carbon tetrachloride, hexane, heptane, cyclohexane, xylene, benzene, dichloroethylene, trichloroethylene, dioxane, diisopropyl ether, tetrahydrofuran and toluene.

9. The process of claim 1 wherein the reaction is conducted at a temperature ranging from 20° C. to 140° C.

10. The process of claim 1 wherein the reaction is conducted at a temperature ranging from 25° C. to 50° C.

11. The process of claim 1 wherein the reaction is conducted at a pressure ranging from 0.096 to 4.83 kg/cm$^2$.

* * * * *